(12) United States Patent
von Oepen

(10) Patent No.: US 8,845,684 B2
(45) Date of Patent: Sep. 30, 2014

(54) TISSUE CLOSURE DEVICE WITH RESILIENT ARMS

(75) Inventor: Randolf von Oepen, Aptos, CA (US)

(73) Assignee: Abbott Cardiovascular Systems, Inc., Santa Clara, CA (US)

( * ) Notice: Subject to any disclaimer, the term of this patent is extended or adjusted under 35 U.S.C. 154(b) by 93 days.

(21) Appl. No.: 13/308,240

(22) Filed: Nov. 30, 2011

(65) Prior Publication Data

US 2013/0138145 A1    May 30, 2013

(51) Int. Cl.
   *A61B 17/08*    (2006.01)
(52) U.S. Cl.
   USPC .......................... 606/216; 606/206; 606/213
(58) Field of Classification Search
   USPC ........ 606/113–114, 127–128, 148–149, 198, 606/205–211, 213, 51–52, 215–216, 139, 606/142–143, 151, 157; 294/100; 81/3.4–3.44, 452–453
   See application file for complete search history.

(56) References Cited

U.S. PATENT DOCUMENTS

| | | | | | |
|---|---|---|---|---|---|
| 714,989 | A | * | 12/1902 | Worthington | 294/86.14 |
| 855,280 | A | * | 5/1907 | Campbell | 279/50 |
| 987,173 | A | * | 3/1911 | Sale | 294/100 |
| 2,137,710 | A | * | 11/1938 | Anderson | 606/206 |
| 2,212,013 | A | * | 8/1940 | Devareaux | 294/100 |
| 2,549,731 | A | * | 4/1951 | Wattley | 439/482 |
| 2,553,479 | A | * | 5/1951 | Schmarje et al. | 81/443 |
| 3,481,641 | A | * | 12/1969 | Berger et al. | 294/100 |
| 3,844,291 | A | * | 10/1974 | Moen | 606/206 |
| 4,085,743 | A | * | 4/1978 | Yoon | 606/140 |
| 4,174,715 | A | * | 11/1979 | Hasson | 606/206 |
| 4,393,872 | A | * | 7/1983 | Reznik et al. | 604/264 |
| 4,467,802 | A | * | 8/1984 | Maslanka | 606/206 |
| 4,990,152 | A | * | 2/1991 | Yoon | 606/140 |
| 4,994,079 | A | * | 2/1991 | Genese et al. | 606/206 |
| 5,002,323 | A | * | 3/1991 | Idsund | 294/100 |
| 5,258,005 | A | * | 11/1993 | Christian | 606/205 |
| 5,407,243 | A | * | 4/1995 | Riemann | 294/100 |
| 5,499,997 | A | * | 3/1996 | Sharpe et al. | 606/206 |
| 5,514,148 | A | * | 5/1996 | Smith, III | 606/151 |
| 5,628,757 | A | * | 5/1997 | Hasson | 606/148 |
| 5,782,861 | A | * | 7/1998 | Cragg et al. | 606/216 |
| 6,991,634 | B2 | * | 1/2006 | Sugiyama et al. | 606/142 |
| 7,137,988 | B2 | * | 11/2006 | Frye | 606/147 |
| 7,261,725 | B2 | * | 8/2007 | Binmoeller | 606/151 |

(Continued)

FOREIGN PATENT DOCUMENTS

EP          607594 A2 *  7/1994

OTHER PUBLICATIONS http://dictionary.reference.com/browse/integral, definition of hte term integral retrieved on Jan. 26, 2012.*

*Primary Examiner* — David Eastwood
(74) *Attorney, Agent, or Firm* — Workman Nydegger; Randy Shen

(57) ABSTRACT

A tissue closure device includes a main body, a sheath, and a biasing member. The main body has a plurality of resilient arms that each extend from a proximal end to a distal tip. The resilient arms are movable between an open configuration in which the distal tips are radially spaced apart from the longitudinal axis of the main body and from each other and a closed configuration in which the distal tips abut one another at or near the longitudinal axis. The sheath is longitudinally slideable on the main body to move the arms between the open and closed configurations. The biasing member causes the sheath to bias the arms toward the closed configuration.

24 Claims, 5 Drawing Sheets

(56) References Cited

U.S. PATENT DOCUMENTS

| | | | |
|---|---|---|---|
| 7,901,428 B2* | 3/2011 | Ginn et al. | 606/213 |
| 7,918,873 B2* | 4/2011 | Cummins | 606/219 |
| 8,057,490 B2* | 11/2011 | Harris et al. | 606/139 |
| 8,100,921 B2* | 1/2012 | Harris et al. | 606/139 |
| 8,142,450 B2* | 3/2012 | Harris et al. | 606/139 |
| 8,152,822 B2* | 4/2012 | Gayzik | 606/151 |
| 8,414,600 B2* | 4/2013 | Harris et al. | 606/139 |
| 2003/0109890 A1* | 6/2003 | Kanner et al. | 606/142 |
| 2008/0315605 A1* | 12/2008 | Shih | 294/100 |
| 2008/0319455 A1* | 12/2008 | Harris et al. | 606/139 |
| 2010/0016873 A1* | 1/2010 | Gayzik | 606/151 |
| 2012/0083804 A1* | 4/2012 | Skerven | 606/142 |

\* cited by examiner

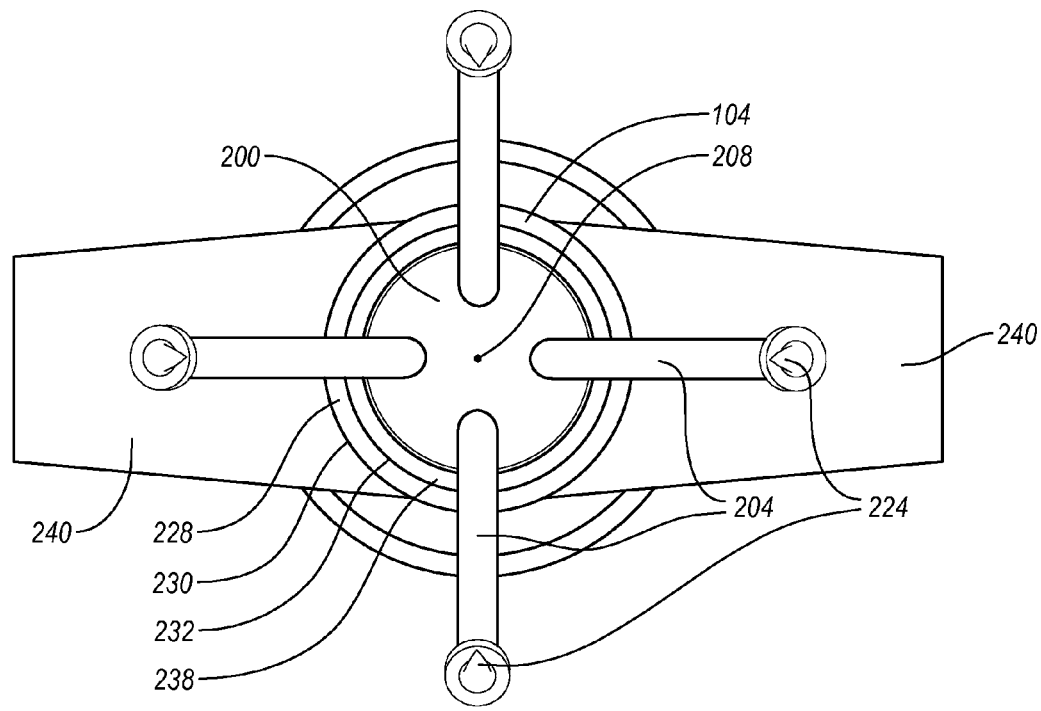
Fig. 2C
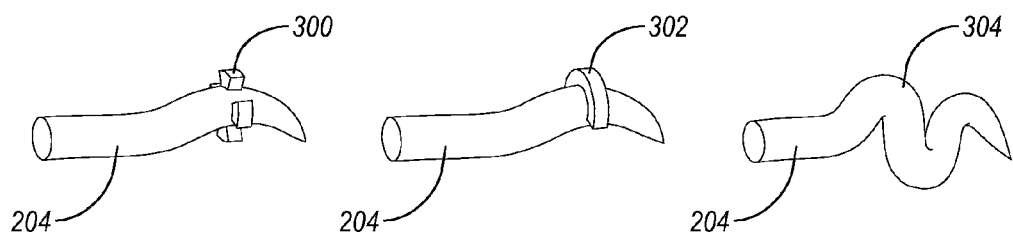
Fig. 3A  Fig. 3B  Fig. 3C

TISSUE CLOSURE DEVICE WITH RESILIENT ARMS

CROSS-REFERENCE TO RELATED APPLICATIONS

Not Applicable.

BACKGROUND OF THE INVENTION

1. The Field of the Invention

The present disclosure generally relates to tissue closure apparatuses and methods.

2. The Relevant Technology

During intravascular and other related medical procedures, catheters are typically inserted through an incision or puncture in the skin and underlying tissues to access an artery or vein, typically in the groin, neck, or subclavian areas of a patient. The catheter can be inserted through a puncture in the blood vessel and guided to the desired site to perform interventional procedures such as angiography, angioplasty, stent delivery, plaque removal, and infusion of a therapeutic substance.

Often these procedures are performed by inserting a hollow needle through a patient's skin and muscle tissue into the vascular system. A guide wire then is passed through the needle lumen into the patient's blood vessel. The needle is removed and an introducer sheath is advanced over the guide wire into the vessel. The catheter typically is passed through the lumen of the introducer sheath and advanced over the guide wire into position for the medical procedure.

After the procedure is completed and the catheter and introducer sheath are removed from the patient, however, the access hole must be closed to prevent hemorrhage. This is typically achieved by applying pressure over the blood vessel manually and then by applying a pressure bandage or a compressive weight. With conventional methods, the rate of post-puncture hemorrhage is high, which can cause considerable complications. This impediment is exacerbated by the concomitant use of anticoagulant medications such as heparin or warfarin and by anti-platelet drugs, which are commonly used following a procedure in order to prevent clot formation and thrombus and/or to treat vascular disease.

It is generally recognized that many currently employed vascular sealing methods and devices and other tissue closure methods and devices incompletely seal holes or wounds in vascular or other tissue. Achieving complete wound closure is particularly important in sealing arterial punctures, which are relatively high pressure systems. For example, under normal blood pressure, the arterial system has a pressure of about 120/80 mmHg or more. Failure to completely close arterial holes can result in hematoma, exsanguination, and other catastrophic consequences, including limb amputation and death. Moreover, many currently employed vascular devices employ methods and materials that remain on the intravascular endothelial surface or otherwise in the sealed vessel. Materials that remain intravascularly can be a nidus for thrombus or intravascular mural hyperplasia with later spontaneous and catastrophic closure of the vessel.

BRIEF SUMMARY

The present disclosure provides methods and apparatuses that are suitable for closure of vascular punctures or other openings in bodily tissues. The devices and methods described herein are configured for wound closure on the external surface of the wound, which allows wound healing with little endothelial disruption thereby reducing the chances of intravascular thrombosis or embolism or intimal hyperplasia.

In one aspect of the invention there is provided a closure device for engaging tissue that includes a main body, a sheath, and a biasing member. The main body has a plurality of resilient arms that each extend from a proximal end to a distal tip. The resilient arms are movable between an open configuration, in which the distal tips are radially spaced apart from the longitudinal axis of the main body and from each other, and a closed configuration, in which the distal tips abut one another at or near the longitudinal axis. The sheath is longitudinally slideable on the main body to move the arms between the open and closed configurations. The biasing member biases the sheath, and thus the arms, toward the closed configuration.

In another aspect of the invention there is provided a method of closing an opening in a body tissue using a closure device having a plurality of resilient arms. The method includes the steps of: moving tips of the resilient arms from a closed configuration in which the tips abut each other to an open configuration in which the tips are radially spread apart from each other; moving the closure device distally toward the tissue while the resilient arms are in the open configuration until the tips penetrate the tissue around the opening; gathering the tissue around the opening by moving the tips of the resilient arms radially inward to the closed configuration; and disengaging the resilient arms from the tissue.

These and other embodiments and features of the present invention will become more fully apparent from the following description and appended claims, or may be learned by the practice of the invention as set forth hereinafter.

Embodiments of the present invention may provide several advantages over conventional designs. For example, embodiments of a closure device according to the present invention may provide an improved, more complete closure of a tissue opening than prior designs. Furthermore, embodiments of a closure device according to the present invention are completely removed from the body after the tissue opening has been closed. This may result in fewer complications and prevent problems of reaccessing patients for multiple procedures. Other advantages may also be provided by embodiments of the present invention.

BRIEF DESCRIPTION OF THE DRAWINGS

Various embodiments of the present invention will now be discussed with reference to the appended drawings. It is appreciated that these drawings depict only typical embodiments of the invention and are therefore not to be considered limiting of its scope. In the drawings, like numerals designate like elements.

FIGS. 3A-3C are perspective views of various embodiments of tissue stops according to the present invention;

DETAILED DESCRIPTION

As used in the specification and appended claims, directional terms, such as "top," "bottom," "up," "down," "upper," "lower," "proximal," "distal," and the like are used herein solely to indicate relative directions in viewing the drawings and are not intended to limit the scope of the claims in any way.

The present disclosure provides methods and apparatuses that are suitable for closure of vascular punctures or other openings in bodily tissues. The devices and methods described herein are configured for wound closure on the external surface of the wound, which allows wound healing with little endothelial disruption thereby reducing the chances of intravascular thrombosis or embolism or intimal hyperplasia.

Generally, the apparatuses and methods described herein can be used with any type of body tissue that has sufficient strength to be held together by the tissue closure devices described hereinafter. By way of example only, embodiments of the present invention can be used to close openings in tissues that have a wall or membrane function, e.g, pulmonary, intestinal, vascular, urethral, gastric, renal or other wall structures, or in membranes, e.g., amniotic or pericardial membranes. Openings in other types of tissues can also be closed using embodiments of the present invention. Although many types of body tissue can be closed by the methods and apparatuses disclosed herein, the description included herein refers to "vessels" for convenience.

Furthermore, the apparatuses and methods described herein can be used with large and small hole punctures or other openings in the body tissue. By way of example, the tissue engaging devices of the present invention can be sized to close holes from 5 French to 30 French or larger. It may also be possible to close holes of other sizes.

Figure 1:
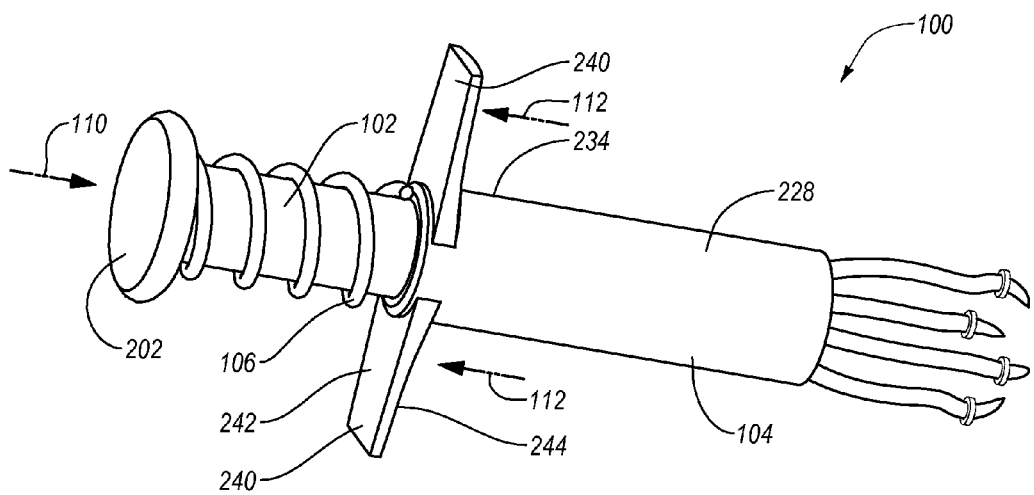
FIG. 1 is a perspective view of a tissue closure device according to one embodiment of the present invention.

Turning now to the drawings, FIG. 1 shows a first embodiment of a tissue closure device 100 for closing an incision, puncture, or other passage or opening through tissue, such as, e.g., communicating with a blood vessel or other body lumen. Tissue closure device 100 includes a main body 102, with a sheath 104 and a biasing element 106 mounted thereon.

Figure 2A:
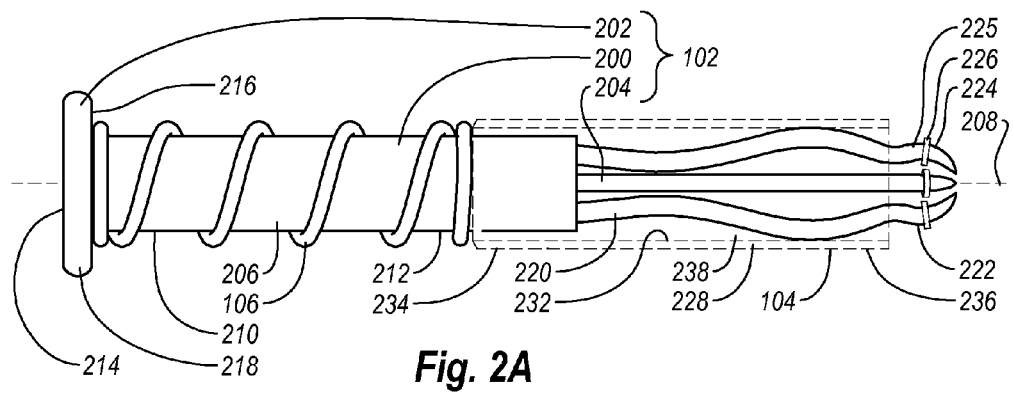
FIGS. 2A and B are side views of the tissue closure device of FIG. 1 in a closed configuration and an open configuration, respectively.
Figure 2B:
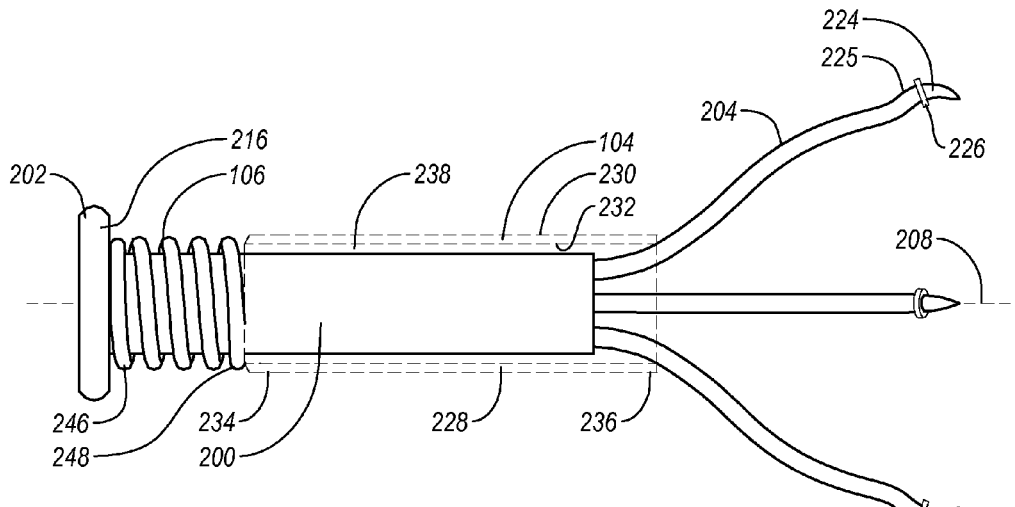
FIG. 2C is an end view of the tissue closure device of FIG. 1 in the open configuration.

Turning to FIGS. 2A-2C, main body 102 comprises a shaft 200 extending along a longitudinal axis 208, with a cap 202 at one end of shaft 200, and a plurality of arms 204 extending from the other end of shaft 200. Shaft 200 can be made of metal, polymeric material, or other rigid material. Furthermore, shaft 200 can be hollow or solid.

Cap 202 has a proximal end face 214 and an opposing distal face 216 with a perimeter sidewall 218 extending therebetween. Cap 202 is longitudinally positioned so that distal face 216 thereof is fixed to a proximal end 210 of shaft 200. Cap 202 can be integrally formed with shaft 200 or connected thereto, e.g., by threaded connection, adhesive, or other fastening device or method known in the art. Cap 202 can be made of similar types of materials as shaft 200.

Arms 204 are fixed to and extend distally from a distal end 212 of shaft 200. Each arm 204 is comprised of a resilient material that extends from a proximal end 220 to a spaced apart distal end 222. Proximal end 220 of each arm 204 is fixed to distal end 212 of shaft 200. Arms 204 can be integrally formed with shaft 200 or connected thereto, e.g., by threaded connection, adhesive, or other fastening device or method known in the art. Each arm 204 can be substantially straight or arcuately shaped, as particularly shown in FIG. 2B. Other shapes are also possible.

A terminating tip 224 is positioned at distal end 212 of each arm 204. Each tip 224 is configured to penetrate tissue and, in conjunction with the tips of the other arms 204, to gather the tissue about an opening in the tissue, as discussed in more detail below. Tip 224 faces distally, but can also face somewhat radially inward, if desired. Each tip 224 can be integrally formed with or attached to the rest of arm 204. Distal end 212 can have a further arched region 225 if desired to prevent sheath 104 from being unintentionally completely slid over distal end 212 of arms 204 and removed from main body 102, as discussed below.

A tissue stop 226 may be positioned on each arm 204 proximal to tip 224 to limit the penetration of tip 224 into the tissue. Tissue stop 226 can also be configured to prevent sheath 104 from unintentionally moving beyond distal end 212 of arms 204, as discussed below. Tissue stop 226 extends radially outward from arm 204. Tissue stop 226 can completely radially encircle arm 204 or a portion thereof. Furthermore, tissue stop 226 can comprise a single contiguous portion or a number of smaller portions that are radially spaced apart. Tissue stop 226 can be integrally formed with arm 204 or attached thereto. In the depicted embodiment, tissue stop 226 completely encircles and is integrally formed with each arm 204. Arched region 225 can also provide spacing for tissue stops 226 when arms 204 are pushed inward, as discussed below.

FIG. 3A-3C depict various embodiments of tissue stops that can be used on arms 204. It should be appreciated that the tissue stops shown in FIGS. 3A-3C are exemplary only and that other types of tissue stops are also envisioned by the present application. FIG. 3A shows a tissue stop 300 that comprises a number of individual portions that are radially spaced apart in the general shape of an "x". FIG. 3B shows a tissue stop 302 that only encircles a portion of arm 204. If each tissue stop 302 is positioned only on the radial outer edge of its corresponding arm 204 (i.e., facing away from longitudinal axis 208), the inner edges of arms 204 remain free of inward projections. As such, the radial inner edges of arms 204 can come together much closer when arms 204 are pushed inward than when arms 204 have tissue stops that project radially inwardly. As a result, this embodiment can be used, e.g., when it is desired to bring arms 204 as close together as possible when pushed inward. FIG. 3C shows a tissue stop 304 that is formed by bending a portion of arm 204. Arm 204 can be bent in any direction desired to form tissue stop 304. Other types of tissue stops can also be used. Of course, if desired, arms 204 can alternatively be free of tissue stops.

Returning to FIGS. 2A-2C, each arm 204 is comprised of a resilient material that allows the arm to move between a closed position in which tip 224 is radially positioned at or near longitudinal axis 208, and an open position in which tip 224 is radially positioned substantially further away from longitudinal axis 208, as noted above. FIGS. 2A and 2B respectively depict arms 204 in the closed and open positions. In one embodiment, arms 204 are resiliently biased toward the open position. That is, without an external force applied to arms 204, arms 204 will move to the open position or remain in the open position if already there. This biasing toward the open position is great enough to overcome the force of tissue pushing inward on the arms in a tissue tract, as discussed below.

Arms 204 can be radially positioned about longitudinal axis 208 so that each arm 204 moves in a substantially different radial direction with respect to longitudinal axis 208 as each arm 204 moves between the closed and open positions. For example, in the open configuration tips 224 can be radially spaced away from longitudinal axis 208 and spaced apart from each other, as particularly shown in FIG. 2C. Because proximal end 220 of each arm 204 is fixed to distal end 212 of shaft 200, proximal ends 220 of all arms 204 remain adjacent to one another in both the closed and opened configurations.

Various numbers of arms 204 can be used in different embodiments of the present invention. For example, in the depicted embodiment, four arms 204 are shown. It is appreciated that two, three, or five or more arms can alternatively be used. For example, in one embodiment six or eight arms are used. Irrespective of the number of arms used, the arms can be generally evenly spaced circumferentially about longitudinal axis 208, as depicted in FIG. 2C.

A guide wire lumen can be included in main body 102 to aid in positioning tissue closure device 100 over the opening in the tissue. For example, a guide wire lumen 227 (FIG. 5A) can extend through cap 202 and shaft 200 along longitudinal axis 208 so as to receive a guide wire that has already been positioned to extend out through the opening in the tissue, as is known in the art.

To move arms 204 of main body 102 between the open and closed configurations discussed above, sheath 104 can be used in conjunction with main body 102. Sheath 104 is depicted in FIGS. 2A and 2B in dashed lines so as to show the structures of shaft 200 and arms 204 positioned therein. Sheath 104 comprises an encircling side wall 228 having an outer surface 230 and an opposing inner surface 232 that extend between a proximal end 234 and a spaced apart distal end 236. Inner surface 232 bounds a lumen 238 that extends longitudinally completely through sheath 104 between proximal and distal ends 234 and 236. Lumen 238 is sized so that shaft 200 and arms 204 of main body 102 can be slidingly received therein.

Returning to FIG. 1, sheath 104 can also include a pair of finger flanges 240 to aid in the use thereof. Each finger flange 240 comprises a proximal surface 242 and an opposing distal surface 244 extending radially outward from opposite sides of sidewall 228 at proximal end 234. Finger flanges 240 are used in conjunction with cap 202 to aid in the manual manipulation of sheath 104, as discussed in more detail below. Sheath 104 can be made of metal, rigid polymerics, or other rigid material.

Sheath 104 is positioned on main body 102 so as to radially encircle shaft 200 and is slideable thereon between a proximal position and a distal position. When sheath 104 is in the proximal position depicted in FIG. 2B, arms 204 extend from lumen 238 at distal end 236 and are positioned in the open configuration. Because each arm 204 is resiliently biased to the open position, arms 204 will remain in the open configuration while sheath 104 is positioned in the proximal position.

When sheath 104 is in the distal position depicted in FIG. 2A, arms 204 are received within lumen 238 so as to be in the closed configuration. As sheath 104 moves distally from the proximal position shown in FIG. 2B to the distal position shown in FIG. 2A, inner surface 232 of sidewall 228 contacts and pushes radially inward on each arm 204. As sheath 104 is moved further distally, arms 204 are continually forced inward towards each other. This continual inward force on arms 204 causes tips 224 disposed at distal ends 222 to move radially inward toward longitudinal axis 208, until arms 204 arrive at the closed configuration shown in FIG. 2A. Because of the inward force of inner surface 232 on arms 204, arms 204 will remain in the closed configuration as long as sheath 104 is positioned in the distal position. In one embodiment, the arched regions 225 at distal ends 212 of arms 204 bias against distal end 236 of sheath 104 when sheath 104 is in the distal position, thereby preventing sheath 104 from moving further distally.

If desired, sheath 104 can be biased toward the distal position so that arms 204 will remain in the closed configuration until a manual proximal force is placed on sheath 104. To bias sheath 104 in the distal position, biasing element 106 can be used. For example, in the depicted embodiment, biasing element 106 comprises a compression spring positioned on shaft 200 of main body 102 between cap 202 and proximal end 234 of sheath 104. Compression springs are designed to store energy as they are compressed so that when the compression force is removed, the compression springs returns to their uncompressed states.

Compression spring 106 comprises one or more helical coils that encircle shaft 200 and extends from a proximal end 246 to a distal end 248. Proximal and distal ends 246 and 248 of compression spring 106 respectively contact and bias against distal face 216 of cap 202 and proximal end 234 of sheath 104. As such, compression spring imposes a separating force between cap 202 and sheath 104. Compression spring 106 is designed to position sheath 104 in the distal position shown in FIG. 2A and discussed above when no compression force acts on the spring. As such, when no external compression force acts on spring 106, spring 106 causes sheath 104 to slide distally with respect to cap 202 so as to slide over the arms 204 of main body 102, thereby positioning arms 204 in the closed configuration, as discussed above. Spring 106 also causes sheath 104 to remain in the distal position until a sufficient external compression force acts on spring 106. Compression spring 106 is but one example of a biasing member that can be used in the present invention. Alternatively, other types of springs, such as a tension spring, a flat spring, a wave spring, etc. can be used. Furthermore, a non-spring device, such as a rubberized material or the like can also be used. Other types of biasing member can also be used.

To move sheath 104 proximally, a proximal compression force is exerted on sheath 104 with respect to main body 102. In one embodiment, this can be accomplished manually by using finger flanges 240 and cap 202, as shown in FIG. 1. A user can position a thumb on proximal end face 214 of cap 202 and two fingers on distal surfaces 244 of finger flanges 240 and provide a compression force (denoted by arrows 110 and 112) between the thumb and fingers which will move sheath 104 proximally to the proximal position shown in FIG. 2B. As sheath 104 moves to the proximal position, distal end 236 of sheath 104 retracts proximally from arms 204. As a result, inner surface 232 of sheath 104 no longer provides an inward force against the portions of arms 204 extending out from lumen 238. As a result, arms 204 move toward the open configuration due to the biasing nature of arms 204, discussed above. When sheath 104 is fully retracted to the proximal position, arms 204 are radially positioned in the open configuration shown in FIG. 2B.

Figure 4:
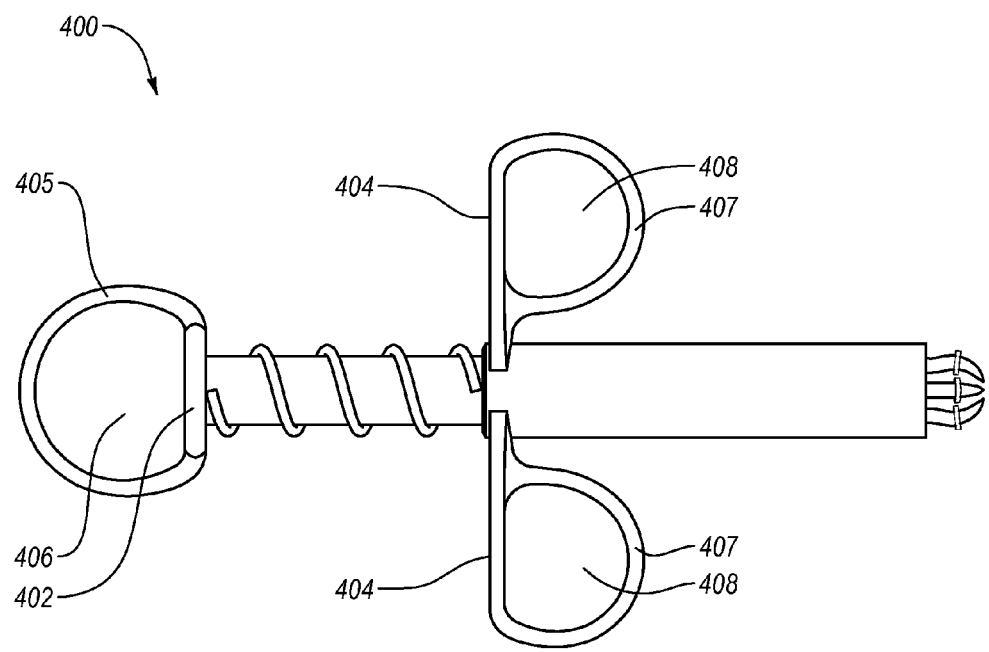
FIG. 4 is a side view of a tissue closure device according to an alternative embodiment.

FIG. 4 depicts an alternative embodiment of a tissue closure device 400 having an alternative cap 402 and finger flanges 404. Cap 402 includes an annular sidewall 405 bounding a thumb opening 406 extending laterally therethrough to provide additional help in gripping cap 402 during manual manipulation of tissue closure device 400. Similarly, each finger flange 404 includes an annular sidewall 407 bounding a finger opening 408 extending laterally therethrough to provide additional help in gripping sheath 104 during manual manipulation of tissue closure device 400. During manual use, the user can place his thumb and fingers respectively through thumb opening 406 and finger openings 408 to more easily provide the compression force required to move sheath 104 to the proximal position.

Figures 5A, 5B:
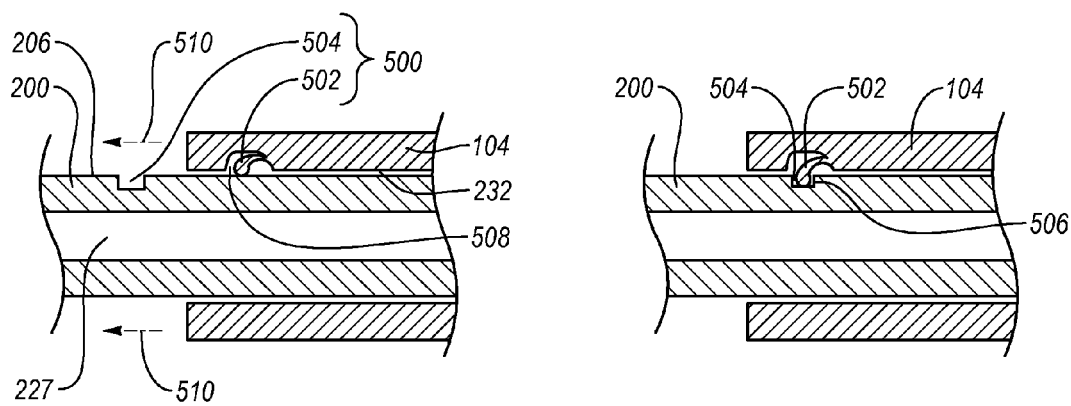
FIGS. 5A and 5B are cross sectional side views of a portion of a tissue closure device showing one embodiment of a locking mechanism.

If desired, a locking mechanism can be used to cause sheath 104 to remain in the proximal position until unlocked. For example, FIGS. 5A and 5B depict one embodiment of a locking mechanism 500 that can be used. Locking mechanism 500 comprises a resilient tab 502 positioned on the inner surface 232 of sheath 104 and configured to be received on a corresponding catch 504 formed on an outer surface 206 of shaft 200. Tab 502 is positioned within a recess 508 formed on inner surface 232 and is biased to move radially inward from inner surface 232. When sheath 104 is positioned on shaft 200 so that tab 502 and catch 504 are not aligned, tab 502 contacts and biases against outer surface 206 of shaft 200, as shown in FIG. 5A. Outer surface 206 can be substantially smooth so that sheath 104 can be slid over shaft 200 with tab 502 biasing against outer surface 206.

As sheath 104 is slid proximally to the proximal position, as depicted by arrows 510 in FIG. 5A, tab 502 becomes aligned with catch 504, as shown in FIG. 5B. When this occurs, the inward bias of tab 502 causes tab 502 to move radially inward into catch 504. The biasing force of tab 502 causes tab 502 to remain in catch 504 until a large enough distal force is applied to sheath 104 to overcome the biasing force. As such, sheath 104 is secured in the open configuration. A lip 506 can be positioned on catch 504 to prevent tab 502 from withdrawing from catch 504 until a sufficient distal force is applied.

To release tab 502 from catch 504, a distal force can be applied to sheath 104 that overcomes the biasing force, thereby causing tab 502 to be released and allow sheath 104 to be moved distally to the distal position. Alternatively, sheath 104 can be rotated or twisted with respect to shaft 200, thereby causing tab 502 to withdraw from catch 504 using a side surface thereof. Also, a lever can be manipulated to release tab 502. Other releasing methods and mechanisms can also be used.

Although tab 502 and catch 504 are depicted as being positioned respectively on sheath 104 and shaft 200, it is appreciated that tab 502 can instead be positioned on shaft 200 and catch 504 on sheath 104. Other types of locking mechanisms can also be used.

Turning to FIGS. 6A-6E, a method of sealing and/or closing a passage through body tissue, such as an opening 600 communicating with a blood vessel or other body lumen 602 through a wall 604 thereof, using tissue closure device 100, will now be discussed. Applicant notes that the disclosed method herein is exemplary only and that other methods of sealing and/or closing a passage through tissue using any of the tissue closure devices envisioned by the present application can also be performed.

Figure 6A:
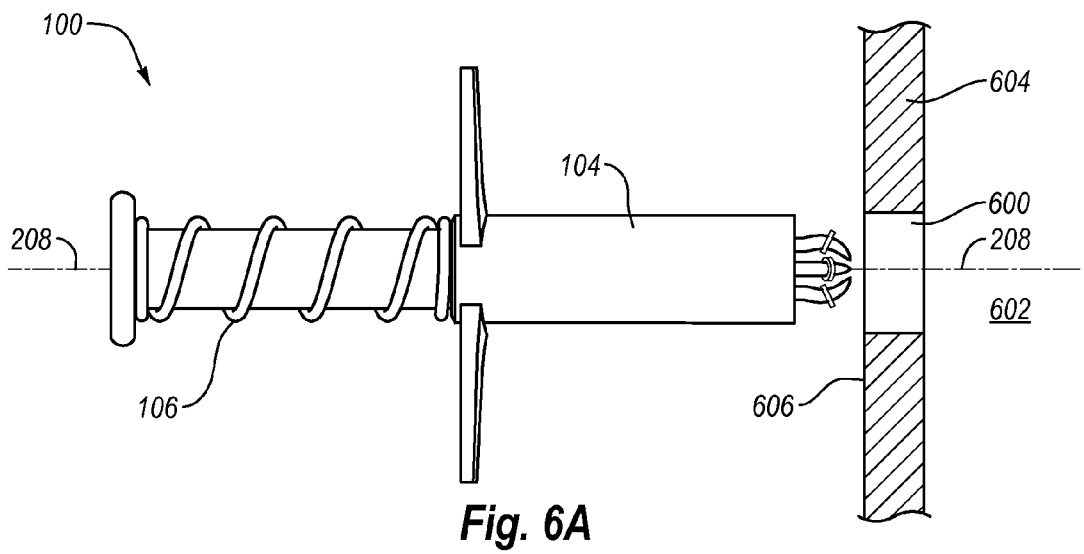
FIGS. 6A-6E illustrate one embodiment of a method of closing an opening in a tissue wall using the tissue closure device of FIG. 1.

Initially, arms 204 of tissue closure device 100 are likely in the closed configuration due to the distal biasing force produced by compression spring 106 on sheath 104, as discussed above. In the closed configuration, tips 224 of arms 204 abut one another at or near longitudinal axis 208 and sheath 104 is at the distal position. While arms 204 are in the closed configuration, tissue closure device 100 is inserted through a tissue tract into the body until tissue closure device 100 is positioned adjacent outer surface 606 of vessel wall 604 and is positioned directly over opening 600 as shown in FIG. 6A. If a guide wire lumen is included in tissue closure device 100, a guide wire can be passed therethrough to aid in positioning tissue closure device 100, as is known in the art.

Figure 6B:
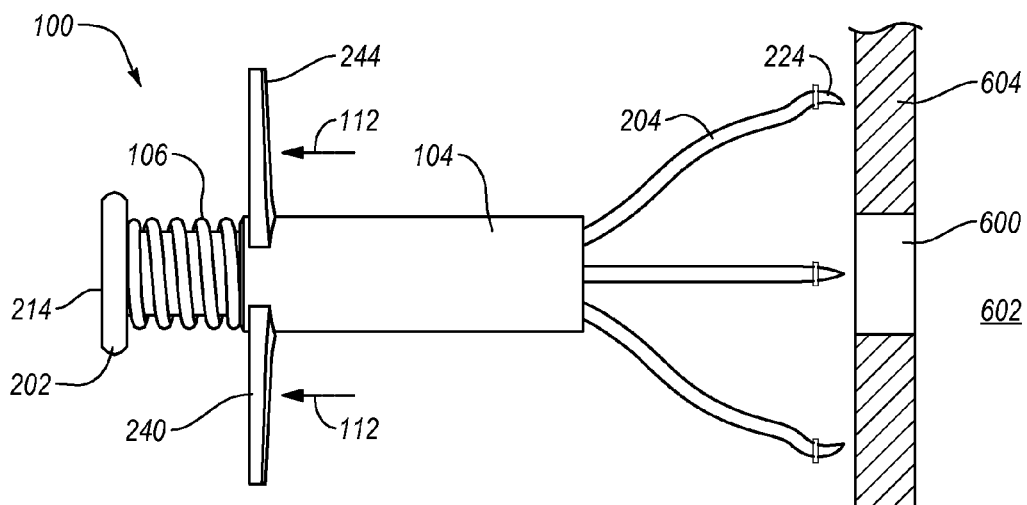

As shown in FIG. 6B, once tissue closure device 100 is in position above opening 600, arms 204 are moved to the open configuration to radially spread apart tips 224 from each other in the tissue tract. This is done by moving sheath 104 from the distal position shown in FIG. 6A to the proximal position shown in FIG. 6B. As noted above, this can be accomplished by positioning the thumb on proximal end face 214 of cap 202 and the fingers on distal surface 244 of finger flanges 240 and compressing the fingers toward the thumb (denoted by arrows 112) with enough force to compress compression spring 106. Sheath 104 can be caused to remain in the proximal position (and thus arms 204 will remain in the open configuration) without further proximal force if a locking mechanism is used, as discussed above. Otherwise, the user can continuously manually compress compression spring 106 for shaft 104 to remain in the proximal position. As noted above, the biasing force that causes arms 204 to move toward the open configuration is great enough to allow arms 204 to move outward despite the inward pressure of the tissue lining the tissue tract.

Figure 6C:
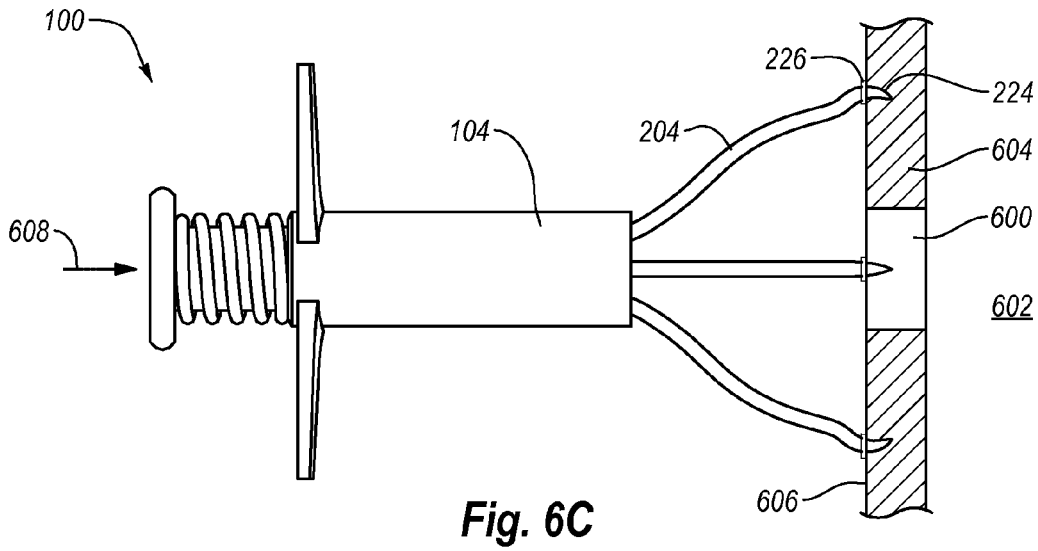

As shown in FIG. 6C, an external distally-directed force, denoted by arrow 608, is then applied to tissue closure device 100 by pushing on tissue closure device 100. The external force 608 causes tips 224 of arms 204 to pierce through outer surface 606 and penetrate into vessel wall 604. Tissue stops 226, if used, bias against outer surface 606 as tips 224 penetrate vessel wall 604, thereby preventing tips 224 from penetrating beyond a specific distance into wall 604.

Figure 6D:
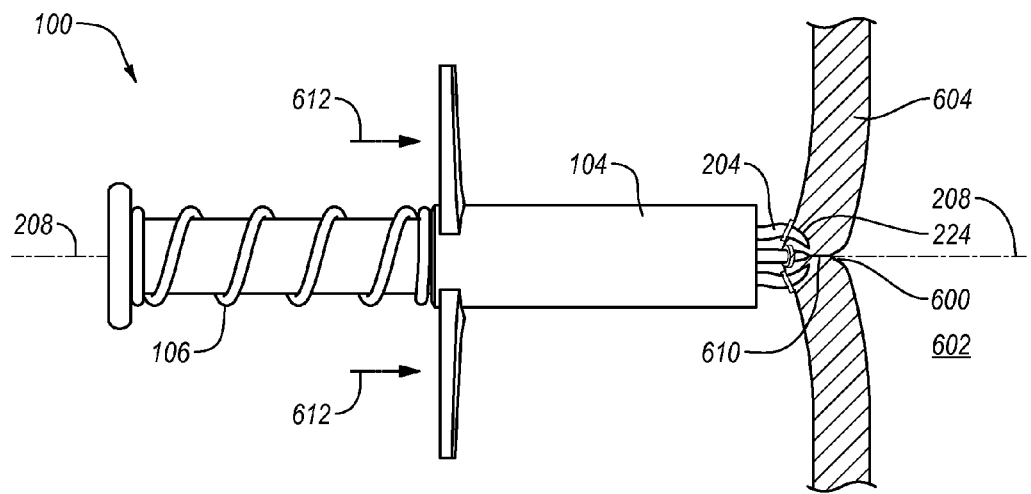

As shown in FIG. 6D, once tips 224 have penetrated vessel wall 604, the tissue around opening 600 is gathered together by moving tips 224 radially inward to the closed configuration. This is done by moving sheath 104 from the proximal position shown in FIG. 6C to the distal position shown in FIG. 6D. Because of the force imposed by compression spring 106 (denoted by arrows 612), sheath 104 automatically moves to the distal position as the user releases or diminishes the compressive force between the thumb and fingers. If a locking mechanism has been used to lock sheath 104 in the proximal position, the locking mechanism is first released, as discussed above. As sheath 104 moves to the distal position, arms 204 move radially inward to the closed configuration, as discussed above. Because of the penetration of tips 224, the tissue surrounding opening 600 is gathered together at longitudinal axis 208, as shown in FIG. 6D, thereby closing opening 600.

Once the tissue has been gathered by tissue closure device 100, tissue closure device 100 can be left in place a sufficient amount of time to allow hemostasis to occur at closed opening 600 by virtue of the gathered tissue 610. Due to compression spring 106, sheath 104 remains in the distal position, thereby causing tips 224 of arms 204 to remain in the closed configuration. As a result, gathered tissue 610 remains gathered.

Figure 6E:
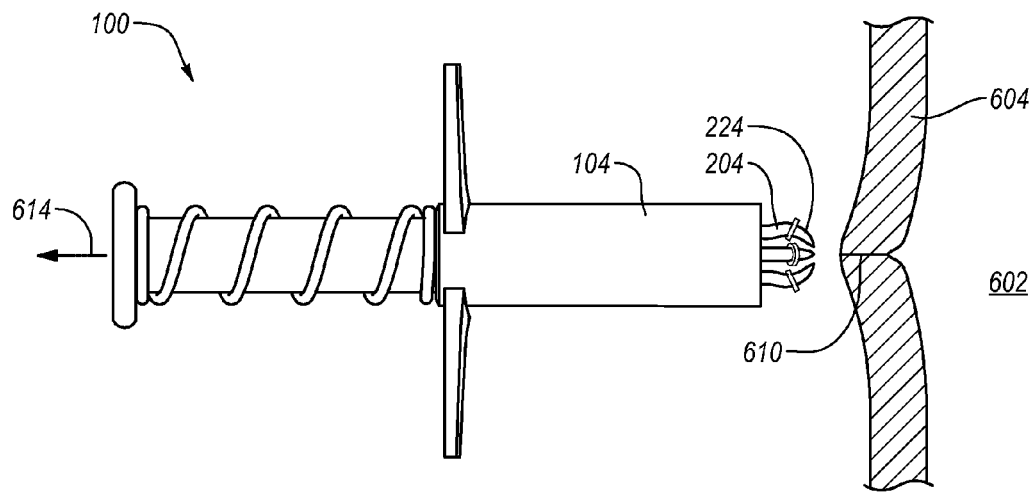

After hemostasis has occurred, tissue closure device 100 can be disengaged from gathered tissue 610. To do this, an external proximally-directed force, denoted by arrow 614, is applied to tissue closure device 100, as shown in FIG. 6E. Force 614 can be accomplished by simply pulling tissue closure device 100 longitudinally away from vessel wall 604. The external force 612 causes tips 224 of arms 204 to disengage from vessel wall 604. If necessary, arms 204 can be partially moved toward the open configuration by moving sheath 104 proximally, as discussed above, to help in disengaging arms 204 from vessel wall 604. Once arms 204 have been disengaged from gathered tissue 610, tissue closure device 100 can be removed from the body.

Although the present invention has been described in considerable detail with reference to certain preferred embodiments, it is contemplated that one skilled in the art may make modifications to the device herein without departing from the scope of the invention. Therefore, the scope of the appended claims should not be considered limited to the embodiments described herein.

What is claimed is:

1. A closure device for closing an opening in body tissue, the closure device comprising:
   a main body having a longitudinal axis, the main body comprising three resilient arms that each extend from a proximal end to a distal tip, the resilient arms being movable between an open configuration, in which the distal tips are radially spaced apart from the longitudinal axis and from each other, and a closed configuration, in which the distal tips abut one another at or near the longitudinal axis;
   a sheath longitudinally slidable on the main body to move the arms between the open and closed configurations; and
   a biasing member that causes the sheath to bias the arms in a first direction toward the closed configuration,
   wherein, each arm of the plurality of arms includes a tissue stop positioned on a distal end of each arm proximal from the tip, a cross-sectional dimension of the arm with the tissue stop at a position of the tissue stop being larger than at a position of the arm proximal from the tissue stop and distal the sheath, the tissue stop comprising a plurality of circumferentially spaced segments positioned about the arm, each arm having a longitudinal axis extending through the arm and the tissue stop, each tissue stop extending radially outward from the longitudinal axis of each arm and the longitudinal axis of the main body and radially encircling at least a portion of each arm.

2. The closure device recited in claim 1, wherein the main body further comprises:
   a shaft extending longitudinally between a proximal end and a distal end, the proximal ends of the plurality of arms being fixed to the distal end of the shaft; and
   a cap fixed to the proximal end of the shaft.

3. The closure device recited in claim 2, wherein the cap is integrally formed with the shaft.

4. The closure device recited in claim 2, wherein the arms are integrally formed with the shaft.

5. The closure device recited in claim 2, wherein the cap includes a thumb opening extending laterally therethrough.

6. The closure device recited in claim 2, wherein the biasing member comprises a helical spring encircling the shaft, the helical spring being positioned on the shaft longitudinally between the cap and the sheath.

7. The closure device recited in claim 6, wherein the helical spring imposes a separating force between the cap and the sheath.

8. The closure device recited in claim 1, wherein the resilient arms are biased toward the open configuration.

9. The closure device recited in claim 1, wherein a guide wire lumen extends longitudinally through the main body.

10. The closure device recited in claim 1, wherein the sheath includes one or more finger flanges extending radially outward therefrom.

11. The closure device recited in claim 10, wherein each finger flange has a finger opening extending therethrough.

12. The closure device recited in claim 1, wherein the sheath has a lumen extending therethrough and the biasing member provides a sufficient force to slide the sheath distally along the main body to at least partially receive the resilient arms within the lumen, thereby moving the arms to the closed configuration.

13. The closure device recited in claim 1, wherein the biasing member comprises a helical spring positioned on the main body.

14. The closure device recited in claim 1, further comprising a locking mechanism to maintain the longitudinal position of the sheath with respect to the main body when the arms are in the open configuration.

15. The closure device recited in claim 14, wherein the locking mechanism comprises:
   a tab positioned on one of the sheath and the main body; and
   a catch positioned on the other one of the sheath and the main body, the catch and tab being positioned so the catch receives and secures the tab when the arms are in the open configuration and releases the tab upon application of a sufficient releasing force.

16. The closure device recited in claim 15, wherein the tab is released by a twisting motion.

17. A method of closing an opening in a body tissue using the closure device of claim 1, the method comprising:
   moving tips of the resilient arms in a first direction from the closed configuration to the open configuration;
   moving the closure device distally toward the tissue while the resilient arms are in the open configuration until the tips penetrate the tissue around the opening until the tissue contacts the tissue stops positioned on the resilient arms;
   gathering the tissue around the opening by moving the tips of the resilient arms radially inward to the closed configuration; and
   disengaging the resilient arms from the tissue.

18. The method recited in claim 17, further comprising removing the closure device from the body.

19. The method recited in claim 17, wherein disengaging the resilient arms from the tissue comprises moving the tips of the resilient arms toward the open configuration.

20. The method recited in claim 17, wherein the body tissue comprises a blood vessel, and wherein disengaging the resilient arms from the tissue is performed after hemostasis of the blood vessel has occurred at the opening.

21. The method recited in claim 17, wherein the resilient arms are at least partially received within a lumen of the sheath in the closed configuration, and wherein moving the tips of the resilient arms from the closed configuration to the open configuration comprises sliding the sheath proximally along the main body to expose the resilient arms, thereby allowing the resilient arms to move radially outward.

22. The method recited in claim 21, wherein the biasing member provides a distal biasing force on the sheath and wherein sliding the sheath proximally along the main body requires a force greater than and opposite to the distal biasing force.

23. The method recited in claim 17, wherein moving the tips of the resilient arms radially inward to the closed configuration comprises sliding the sheath distally along the main body to at least partially receive the resilient arms in a lumen of the sheath, thereby causing the resilient arms to move radially inward.

24. The method recited in claim 23, wherein the biasing member is used to cause the sheath to slide distally along the main body to at least partially receive the resilient arms within the lumen.

* * * * *